United States Patent
Gorin (10) Patent No.: US 8,269,171 B2
(45) Date of Patent: Sep. 18, 2012

(54) SYSTEM AND METHOD FOR DETECTING, TRACKING AND IDENTIFYING A GAS PLUME

(75) Inventor: Brian A. Gorin, Setauket, NY (US)

(73) Assignee: BAE Systems Information and Electronic Systems Integration Inc., Nashua, NH (US)

( * ) Notice: Subject to any disclaimer, the term of this patent is extended or adjusted under 35 U.S.C. 154(b) by 321 days.

(21) Appl. No.: 12/563,628

(22) Filed: Sep. 21, 2009

(65) Prior Publication Data

US 2010/0078561 A1    Apr. 1, 2010

Related U.S. Application Data

(60) Provisional application No. 61/100,476, filed on Sep. 26, 2008.

(51) Int. Cl.
*G01N 21/00* (2006.01)
(52) U.S. Cl. .................................................. 250/338.5
(58) Field of Classification Search .............. 250/338.5
See application file for complete search history.

(56) References Cited

U.S. PATENT DOCUMENTS

| | | | |
|---|---|---|---|
| 5,495,562 A * | 2/1996 | Denney et al. | 345/421 |
| 5,793,889 A * | 8/1998 | Bushman | 382/221 |
| 7,491,944 B1 * | 2/2009 | Stork et al. | 250/390.07 |
| 7,916,947 B2 * | 3/2011 | Conger et al. | 382/181 |
| 7,991,192 B2 * | 8/2011 | Lee et al. | 382/103 |
| 2004/0088113 A1 * | 5/2004 | Spoonhower et al. | 702/2 |
| 2005/0156111 A1 * | 7/2005 | Racca et al. | 250/338.5 |
| 2009/0257622 A1 * | 10/2009 | Wolowelsky et al. | 382/103 |
| 2011/0081040 A1 * | 4/2011 | Conger et al. | 382/100 |

* cited by examiner

*Primary Examiner* — Christine Sung
(74) *Attorney, Agent, or Firm* — Dilworth & Barrese, LLP; Leo G. Lenna; Daniel J. Long (57) ABSTRACT

A system and method for detecting, tracking and identifying a gas plume. The system comprises a processor and a detector in communication with the processor. The detector is effective to detect spectral radiance from a region of interest to detect first and second detected spectral radiance data with a known time difference. A database is in communication with the processor, the database includes a library. The processor is effective to create at least a first image and a second image from the first and second detected spectral radiance data and co-register the first and second images to produce a first co-registered image and a second co-registered image. The processor is further effective to subtract the first co-registered image from the second co-registered image to produce a difference image and generate a cluster region around a difference region in the difference image. The processor is further effective to analyze the spectral radiance from the cluster region to produce a spectral characteristic curve; and correlate the spectral characteristic curve against the library to identify the gas plume.

20 Claims, 8 Drawing Sheets

SYSTEM AND METHOD FOR DETECTING, TRACKING AND IDENTIFYING A GAS PLUME

PRIORITY CLAIM

This application claims priority to U.S. Provisional Patent Application No. 61/100,476 filed Sep. 26, 2008, entitled "Temporal Hyperspectral Change Detection Method for Gas Plume Detection, Tracking and Identification" the entirety of which is hereby incorporated by reference.

BACKGROUND OF THE INVENTION

1. Field of the Invention

This disclosure relates to image processing and, more particularly, to a system and method for identifying a gas plume in a region of interest.

2. Description of the Related Art

Lethal gas plumes often exhibit very low concentration levels of gaseous effluents. If such gases are released in an environment, it is sometimes quite difficult to detect their presence. For example, some highly toxic gases such as Sarin or VX are not visible to the human eye and have low levels of emissions compared with surrounding environments. Prior art techniques exist for creating a digital image of energy emissions from a region of interest and then determining whether a gas is present in the region. Such techniques may include a "push broom" approach where a single spectral radiance image is taken from overhead, perhaps using an airborne platform, in a single pass. That image is then processed a few hours later. The disclosure relates to an improvement over these prior art techniques.

SUMMARY OF THE INVENTION

One embodiment of the invention is a method for detecting and identifying a gas plume. The method comprises receiving, by a processor, a request regarding a region of interest including a gas plume; detecting, by a detector in communication with the processor, spectral radiance from the region of interest to detect first and second detected spectral radiance data; creating, by the processor, at least a first image and a second image from the first and second detected spectral radiance data; co-registering, by the processor, the first and second images to produce a first co-registered image and a second co-registered image; subtracting, by the processor, the first co-registered image from the second co-registered image to produce a difference image; generating, by the processor, a cluster region around a difference region in the difference image; analyzing, by the processor, the spectral radiance from the cluster region to produce a spectral characteristic curve; and correlating, by the processor, the spectral characteristic curve against a library to identify the gas plume.

Another embodiment of the invention is a system for detecting and identifying a gas plume. The system comprises a processor; a detector in communication with the processor, the detector effective to scan a region of interest to detect first and second detected spectral radiance data; a database in communication with the processor, the database including a library; wherein the processor is effective to create at least a first image and a second image from the first and second detected spectral radiance data; co-register the first and second images to produce a first co-registered image and a second co-registered image; subtract the first co-registered image from the second co-registered image to produce a difference image; generate a cluster region around a difference region in the difference image; analyze the spectral radiance from the cluster region to produce a spectral characteristic curve; and correlate the spectral characteristic curve against the library to identify the gas plume.

Yet another embodiment of the invention is a method for detecting and identifying a gas plume. The method comprises receiving, by a processor, a request regarding a region of interest including a gas plume; detecting, by a detector in communication with the processor, spectral radiance from the region of interest in the LWIR range to detect first and second detected spectral radiance data; creating, by the processor, at least a first image and a second image from the first and second detected spectral radiance data, first image and the second image each have two dimensions relating to space and a third dimension relating to wavelength of the spectral radiance; removing, by the processor, elevation effects in the first and second images; co-registering, by the processor, the first and second images to produce a first co-registered image and a second co-registered image, the co-registering includes, for at least one wavelength, lining up temporally adjacent images with the same origin; subtracting, by the processor, the first co-registered image from the second co-registered image to produce a difference image; generating, by the processor, a cluster region around a difference region in the difference image; analyzing, by the processor, the spectral radiance from the cluster region at a particular time to produce a spectral characteristic curve; and correlating, by the processor, the spectral characteristic curve against a gas plume library to identify the gas plume.

BRIEF DESCRIPTION OF THE DRAWINGS

The drawings constitute a part of the specification and include exemplary embodiments of the present invention and illustrate various objects and features thereof.

DETAILED DESCRIPTION OF THE PREFERRED EMBODIMENT(S)

Various embodiments of the invention are described hereinafter with reference to the figures. Elements of like structures or function are represented with like reference numerals throughout the figures. The figures are only intended to facilitate the description of the invention or as a guide on the scope of the invention. In addition, an aspect described in conjunction with a particular embodiment of the invention is not necessarily limited to that embodiment and can be practiced in conjunction with any other embodiments of the invention.

The prior art systems described above do not work well in detecting many gases. Gases frequently have low spectral radiance energy emissions and may be hidden in noisy environments including other elements emitting energy at similar wavelengths. In addition, the backgrounds upon which the gases are imposed change spectral radiance due to temperature changes, changes in the atmosphere, solar and thermal changes, time of day etc. and the gases themselves change in temperature (and thus energy emission) over the course of time. In urban environments, the radiant backgrounds themselves provide even more difficulties in detecting and distinguishing gases from the background. Low temperature differences between the gas plume and a noisy radiant background scene often result in unsuccessful gas detection attempts because of the poor signal to noise ratio. Some prior art techniques attempt to deal with these problems by maintaining massive libraries of backgrounds. However, those libraries can not include all potential variants in temperature, time of day etc. without being cost prohibitive. Some techniques attempt to normalize a region of interest but such techniques result in decreased sensitivity. With some gas plumes having very low concentration levels (parts per million or PPM levels) and therefore very low spectral emission coupled with low temperature, differences between the plumes and the backgrounds being small and changing, such decreases in sensitivity may result in loss of detection.

Figure 1:
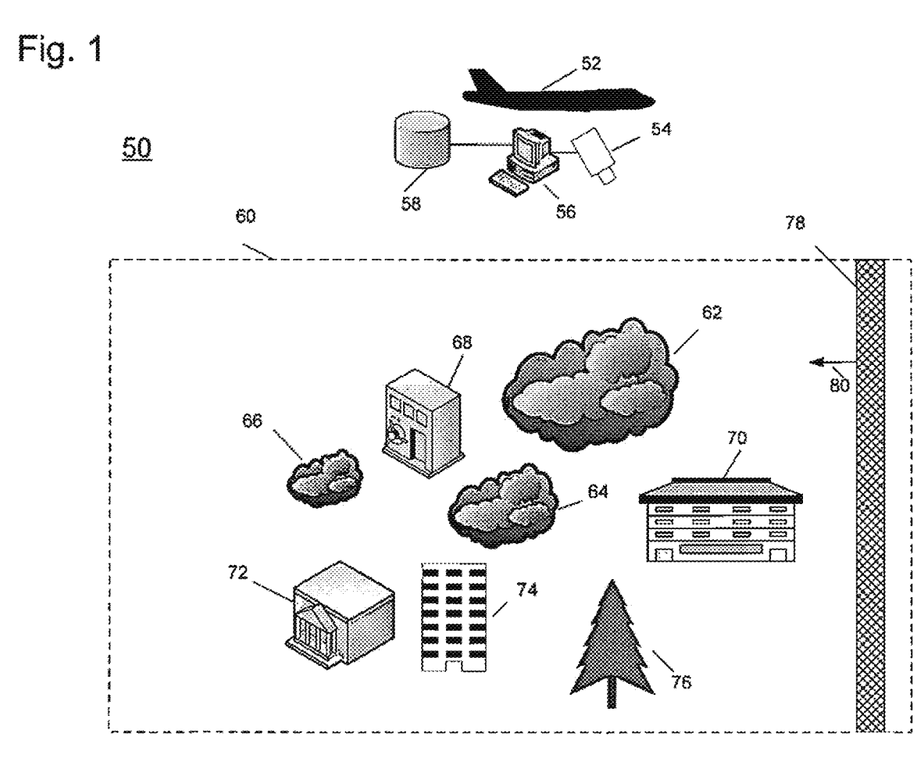
FIG. 1 is a system drawing of a system for identifying a gas plume in accordance with an embodiment of the invention.

Referring to FIG. 1, there is shown a system 50 for identifying a gas plume in accordance with an embodiment of the disclosure. System 50 includes an airplane or airborne platform 52 with a detector 54 such as a long wave infrared (LWIR) detector focal plane array (FPA) like a mercury cadmium telluride HgCdTe detector FPA integrated with a dispersive grating spectrometer. Detector 54 is in communication with a processor 56 which is, in turn, in communication with a database 58. Detector 54 can be used to scan and detect spectral radiance from a region of interest 60. For example, detector 54 may detect LWIR spectral radiance having wavelengths in the range of 7.5 µm to 13.5 µm though any frequency band may be used and benefit from this disclosure. Many gasses have spectral radiance signatures in the LWIR, VNIR (Visible through Near InfraRed), SWIR (Short Wave Infrared) or MWIR (Mid Wave Infrared Spectral) ranges. As shown, region of interest 60 may include gas plumes 62, 64, 66 of unknown characteristics along with a buildings 68, 70, 72, and 74 and a natural growth such as tree(s) 76.

Figure 2:
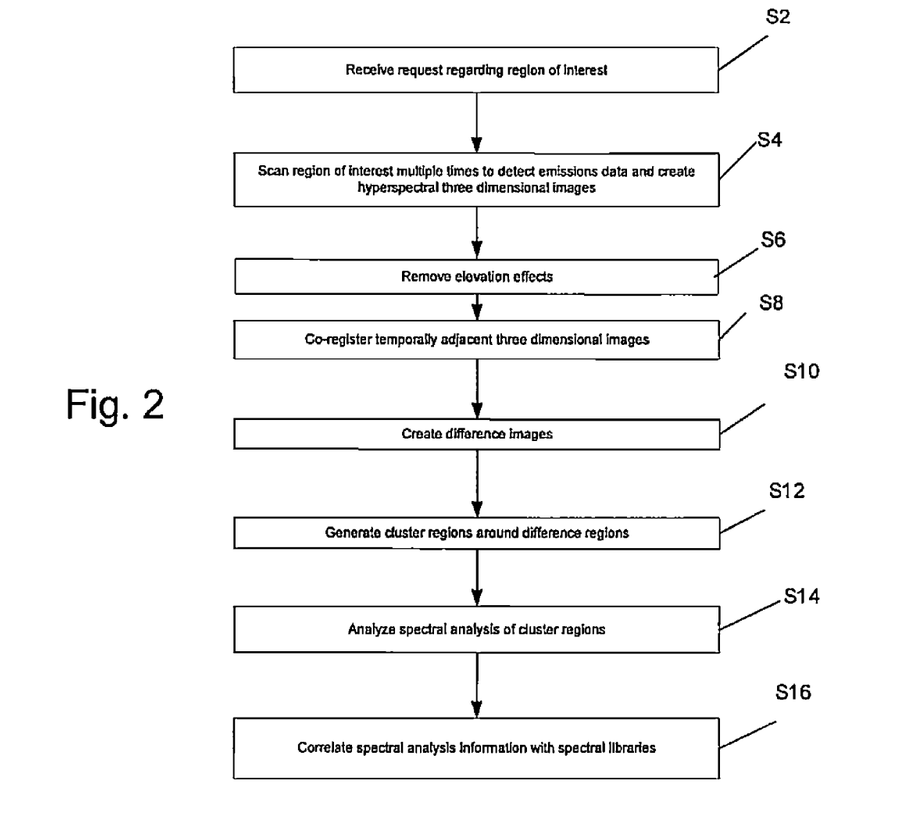
FIG. 2 is a flow chart illustrating a process which could be performed in accordance with an embodiment of the invention.

Referring to FIG. 2, there is shown a process which may be performed by processor 56. As shown, at step S2, a request is received regarding a region of interest including a gas plume. For example, a person on the ground may identify region of interest 60 (FIG. 1).

At step S4, processor 56 controls detector 54 to scan region of interest 60 multiple times with defined time differences, typically on the order of seconds. Referring again to FIG. 1, detector 54 has a field of view (FOV) 78. FOV 78 is scanned (as shown by arrow 80) across region of interest 60 to detect spectral radiance data. The spectral radiance data is used by processor 56 to create two dimensional spatial image data coupled with the spectral radiance data for each spatial pixel to create a three dimensional spectral image cube for region of interest 60. The images need not be displayable to a user and may simply be processed by processor 56. The spatial scanning detects spectral radiance from region of interest 60 at a variety of frequencies f or wavelengths λ. For example if LWIR is used, detector 54 can detect energy information relating to thermally generated spectral radiance. Each scan of region of interest 60 by detector 54 results in processor 56 creating a three dimensional image—two dimensions for space (i.e. X and Y coordinates) and one dimension for wavelength λ. For example, the three dimensional image may be represented as 512 pixels X by 512 pixels Y by 100 pixels λ. Region of interest 60 is scanned multiple times in a short period (e.g. over a few seconds or minutes) while airborne platform 52 passes over region of interest 60. Alternatively, a single field of view 78 may cover the entire region of interest 60 and then that field of view is scanned for each wavelength of interest. A series of temporally adjacent three dimensional images are now created relating to region of interest 60—one for each scan 80.

The scanning could be performed using, for a example, systems available from BAE SYSTEMS such as SPIRITT (Spectral Infrared Remote Imaging Transition Test bed) systems. The LWIR hyperspectral detector as part of SPIRIT, for example, can produce 186 longwave wavelength images for each of the spatial 512 pixels X by 512 pixels Y at 400 frames per second. SPIRITT has five separate sensors with a common aperture so that sensor imagery are all co-registered. Data from multiple sensors within SPIRITT can be fused or used for measuring extended spectral signatures. SPIRITT operates on an inertially stabilized platform resulting in high quality images.

Detection is optimized by collecting light or energy with a large unobstructed fore-optic aperture and focusing the energy with high performance imaging spectrometer optics coupled to focal plane arrays (FPAs) with low-noise electronics. To keep this well-constructed image plane fixed on the FPAs during image integration, a high-performance servo stabilization system controls gimbal motion and enables scanning using high-performance fiber-optic gyros.

Target discrimination is performed in the SPIRITT Hyperspectral Digital Signal Processor (HDSP) weapons replacement assembly (WRA). This assembly receives the extremely high-quality hyperspectral image data from the low-noise focal plane electronics and removes detector artifacts. This step helps ensure that the target discrimination algorithms do not generate false alarms from detector fixed-pattern noise. The HDSP discrimination algorithms operate on the corrected uniform hyperspectral image data. Target cueing is performed by integrating the data from the discrimination algorithms and the geo-location data. Precise geo-location data is developed from the gimbal angle, Inertial Navigation System/Global Positioning System (INS/GPS) and the SPIRITT sensor geometry knowledge.

The SPIRITT sensor uses high-quality focal planes and spectrometers for the visible, near infrared, short infrared, as well as the long wave infrared spectral regions. The Visible Near-Infrared Hyperspectral Imager (VNIR HSI) detector and the Short Wave Infrared (SWIR) detector are coupled to a high-performance Offner spectrometer. When the sensor system is scanned, sequential frames in the spatial dimension along the scan direction are read out at a typical rate of 400 Hz (frames/sec), enabling the system to build up a three dimensional image of hyperspectral data. This implementation develops a spectral profile for each of the spatial pixel locations for the entire scan of the sensor system.

In addition to hyperspectral imagers, the SPIRITT system has two high-resolution imagers. These imagers are optically integrated into the gimbaled system such that they share the common aperture large telescope fore-optics. The SPIRITT system has visible and mid-wave infrared high-resolution imagers.

With each scan, SPIRITT collects concurrent image data from all the focal planes. Visible Near-Infrared (VNIR) high resolution, Mid-Wave Infrared (MWIR) high resolution, VNIR hyperspectral, Short-Wave Infrared (SWIR) and Long-Wave Infrared (LWIR) hyperspectral image data are all co-registered (as discussed below).

At step S6, geopointing is performed where elevation effects relating to the region of interest are removed such as through the use of ortho-rectified map databases. Knowing the latitude and longitude of region of interest 60, digital elevation maps are used to remove elevation effects effectively from georectified images making region of interest 60 flat or two dimensional with respect to space.

At step S8, processor 56 performs co-registration of temporally adjacent three dimensional images or cubes. Referring to FIG. 1, as airborne platform 52 is moving, images generated by processor 56 may relate to different spatial coordinates. Processor 56 performs co-registration of these images in the spatial plane so that data in the plurality of detected spectral images may be compared. For example, each scan 80 of region of interest 60 results in a single two spatial dimensioned image for each wavelength spectral channel centered at λn, where n=1 to m, representing the m spectral channels. During co-registration, all spatial pixels X×Y at a particular time for all of the spectral channels m are registered both spatially and spectrally with temporally adjacent images. The co-registration process is based on spatial information such that equivalent spectral bands are selected to compare groups of matching pixel valves. Once two images are co-registered at one wavelength, those images are co-registered at all wavelengths due to the self-registration of wavelengths for the dispersive spectrometer geometry.

Figure 3:
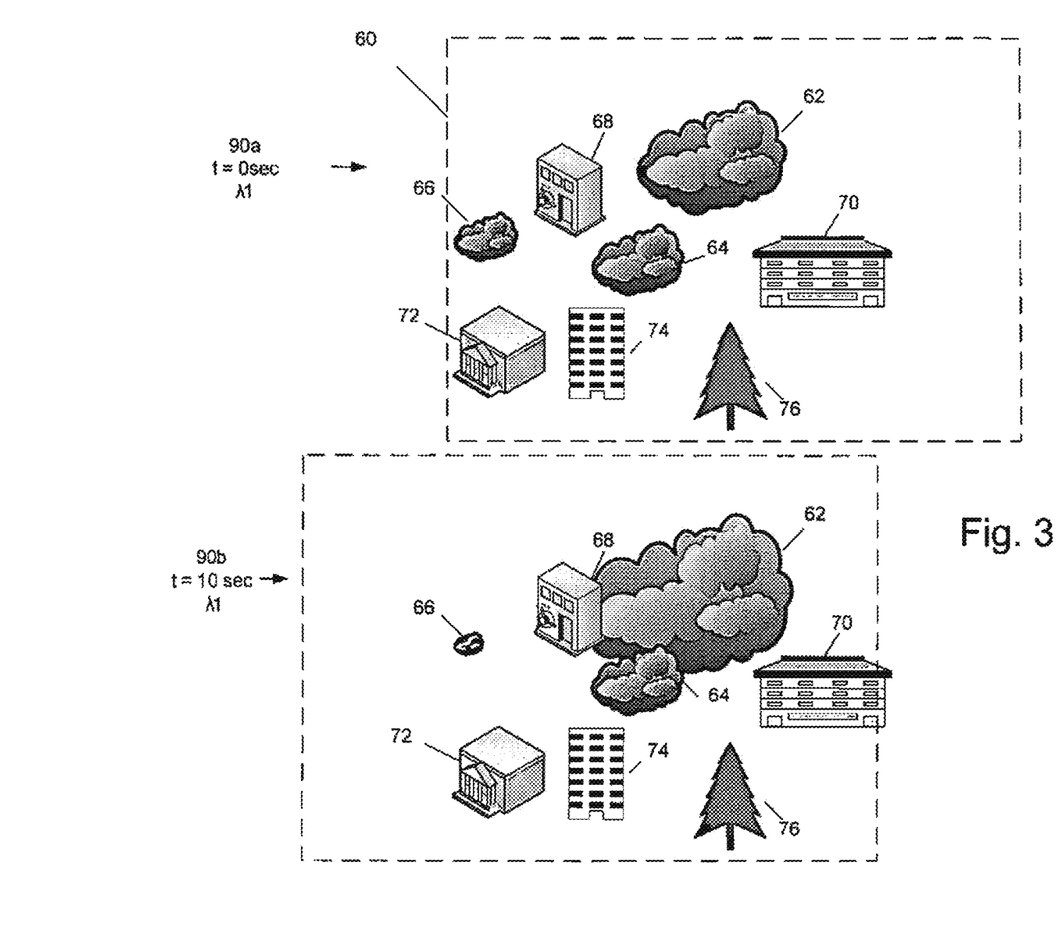
FIG. 3 is an illustration of two images which could be created in a system in accordance with an embodiment of the invention.
Figure 4:
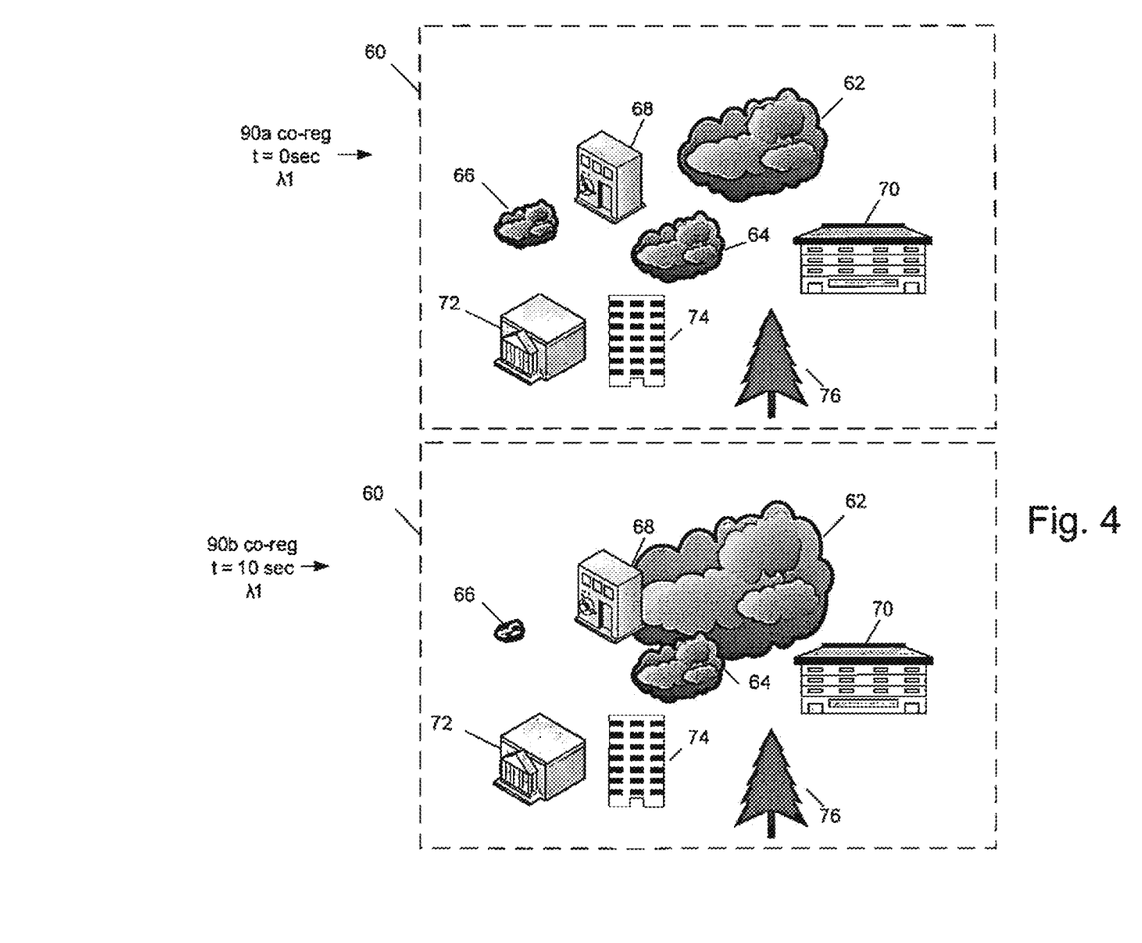
FIG. 4 is an illustration of two images which could be created in a system in accordance with an embodiment of the invention.

For example, FIG. 3 shows two images 90a and 90b created by processor 56 based on spectral radiance detected by detector 54 of region of interest 60. Image 90a was created based on spectral radiance detected by a scan of detector 54 starting at a time t=0 seconds for wavelength λn (where n is sampled from 1 to n) of region of interest 60. Similarly, image 90b was created based on spectral radiance detected by a scan of detector 54 starting at time t=10 seconds also for wavelength λn for region interest 60. In order to compare these images, co-registration is performed. As can be seen, most of the regions have not changed between image 90a and image 90b. Buildings 68, 70, 72, 74 and tree 76 are emitting the same spectral radiance but simply appear at a different location in image 90a and 90b. Gas plume 66 becomes smaller from image 90a to image 90b and gas plume 62 becomes larger from image 90a to image 90b. Gas plume 64 appears to remain the same. Co-registration lines up these two images 90a, 90b so that all regions start from the same spatial origin as shown in FIG. 4 at 90a co-reg and 90b co-reg.

Figure 5:
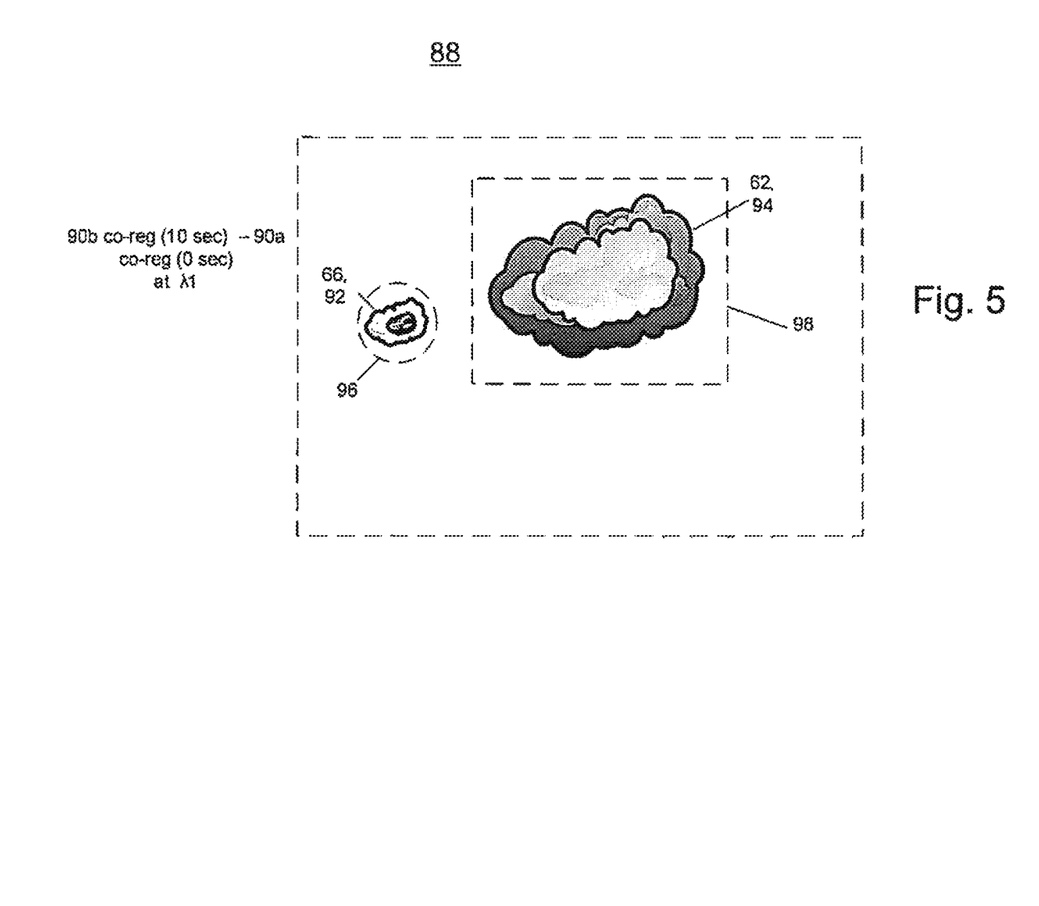
FIG. 5 is an illustration of an image which could be created in a system in accordance with an embodiment of the invention.

Referring again to FIG. 2, now that images 90 have been co-registered, processor 56 at step S10, creates difference images based on temporally adjacent three dimensional images. For example, for every wavelength in a particular range, such as in the LWIR range, processor 56 creates difference images from temporally adjacent images so that spectral radiance changes from one image to the temporally adjacent image may be analyzed. For example, FIG. 5 shows a difference image 88 which is the result of subtracting pixel values in image 90a co-reg from image 90b co-reg (FIG. 4). In difference image 88, pixel information relating to buildings, 68, 70, 72, 74, and tree 76 as well as some parts of gas plumes 62 and 66 are removed because there was no change in these values from image 90a co-reg to image 90b co-reg. Difference image 88 includes difference information 94, 92 relating to differences in pixel values between images 90a co-reg and 90b co-reg for gas plumes 62 and 66. In the example, gas plume 64 is not shown in difference image 88 as gas plume 64 had no relative change from image 90a to image 90b. Processor 56 creates difference images 88 for all temporally adjacent images at each wavelength used by system 50.

Figure 6:
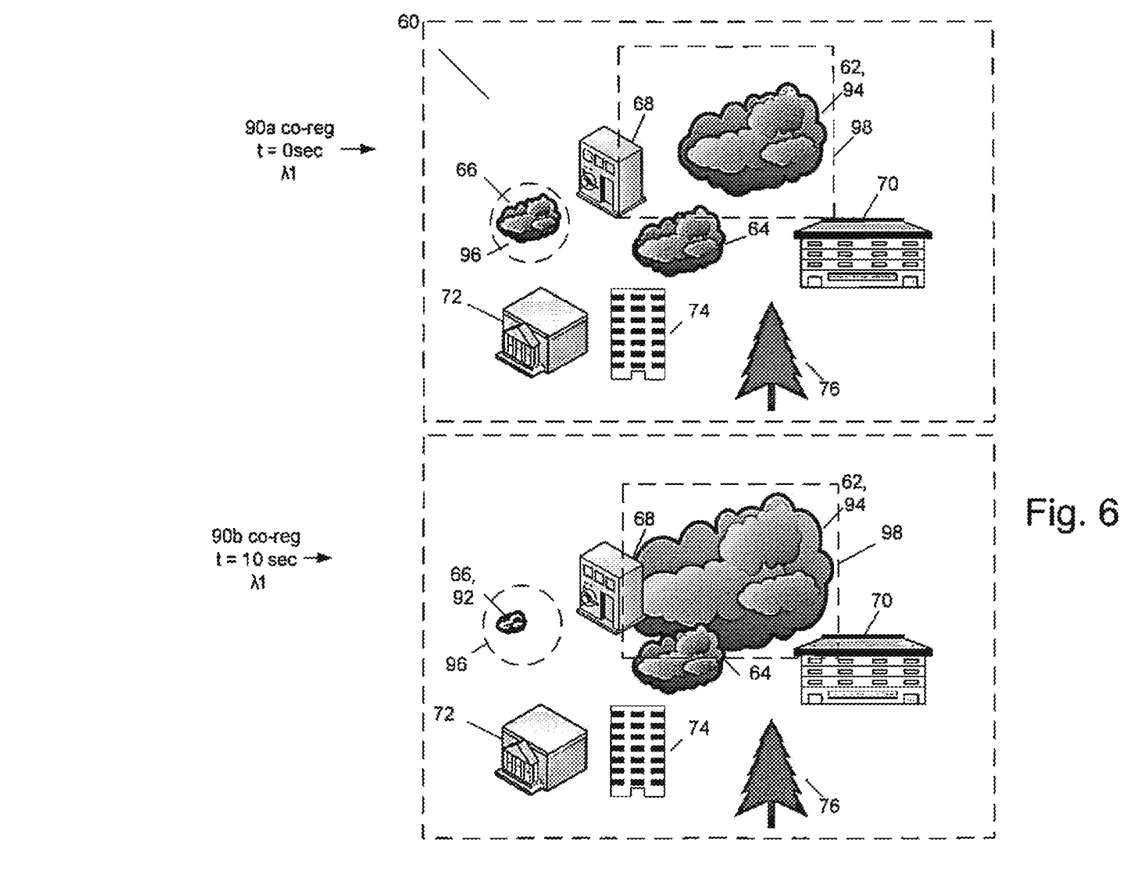
FIG. 6 is an illustration of two images which could be created in a system in accordance with an embodiment of the invention.

At step S12 in FIG. 2, processor 56 generates cluster regions around difference regions in the difference images. For example, as shown in FIG. 5, all of the background images (buildings 68, 70, 72, 74 and tree 76) have been removed because of the subtraction in step S10 resulting in two difference regions 92 and 94 in difference image 88. Processor 56 can now analyze pixels relating to plumes 62 and 66 with difference regions 92 and 94 and identify the pertinent absorption wavelengths and spectral features. Processor 56 generates cluster regions 96, 98 around difference regions 92 and 94. Cluster regions 96, 98 are defined by drawing around difference regions 92 and 94. Now processor 56 proceeds with spectral analysis of these cluster regions within the co-registered images (FIG. 4). FIG. 6 shows cluster regions 96, 98 in co-registered images 90 co-reg.

Figure 7:
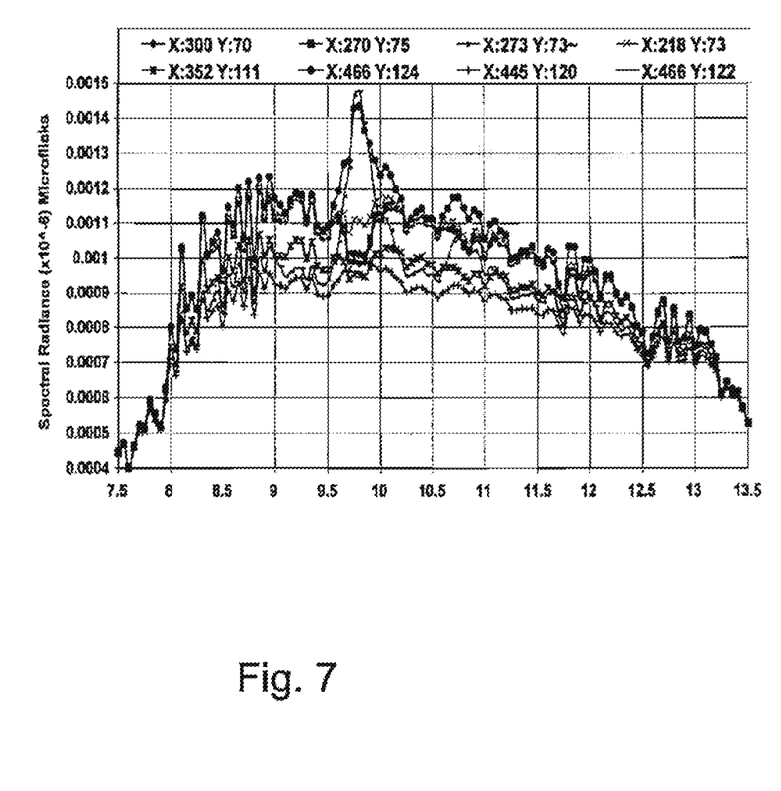
FIG. 7 is a graph showing wavelength and spectral radiance for information which could be generated in accordance with an embodiment of the invention.
Figure 8:
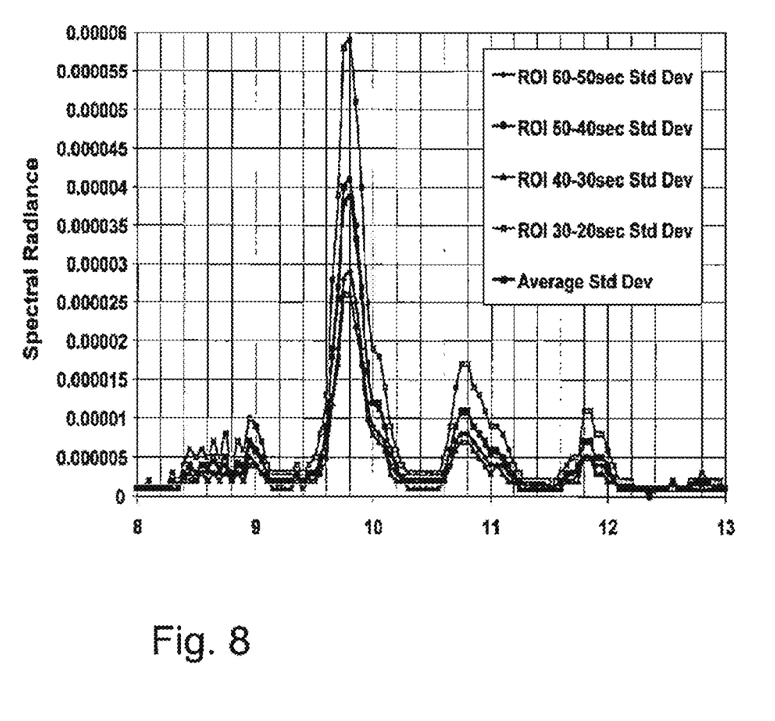
FIG. 8 is a graph showing wavelength and spectral radiance for information which could be generated in accordance with an embodiment of the invention.

At step S14, processor 56 generates statistical sampling of the spectral radiance for cluster regions 96, 98 for desired times and/or desired time differences. For example, for a single scan 80, FIG. 7 shows a graph of wavelength and spectral radiance in microflicks for 8 points with designated X and Y coordinates within example clusters 96, 98. The wavelength range shown is for the LWIR spectral range but could be for any spectral range. Cluster regions 96, 98 may be analyzed by processor 56 over periods of time so that mean and standard deviation values may be determined for region of interest 60 as shown in FIG. 8 for various time differences.

Armed with the spectral analysis information and a spectral characteristic curve, at step S16, processor 56 can now correlate the spectral analysis results with known libraries stored in database 58 (FIG. 1) to identify gas plumes 62, 64, 66. For example, the PNNL (Pacific Northwest National Laboratory) gas plume model library may be used. In this way processor 56 can identify a type of gas in plumes 62, 64, 66 by comparing spectral analysis like the graph shown in FIG. 8 with libraries showing spectral emissions for gases. Processor 56 can also determine tracking of movement of plumes 62, 64, 66 based on prior locations and times of plumes 62, 64, 66.

Although a processor is shown and described, clearly, the algorithms discussed above could be performed using one or many processors.

While the invention has been described with reference to a number of exemplary embodiments, it will be understood by those skilled in the art that various changes can be made and equivalents can be substituted for elements thereof without departing from the scope of the invention. In addition, many modifications can be made to adapt a particular situation or material to the teachings of the invention without departing from essential scope thereof. Therefore, it is intended that the invention not be limited to any particular exemplary embodiment disclosed herein.

What is claimed is:

1. A method for detecting and identifying a gas plume, the method comprising:
    receiving, by a processor, a request regarding a region of interest including a gas plume;
    detecting, by a detector in communication with the processor, spectral radiance from the region of interest to detect first and second detected spectral radiance data;
    creating, by the processor, at least a first image and a second image from the first and second detected spectral radiance data;

co-registering, by the processor, the first and second images to produce a first co-registered image and a second co-registered image, comprising:
   a) selecting a spectral wavelength;
   b) performing a pixel level comparison of the first and second images for the selected spectral wavelength to determine if an equivalent spectral wavelength value exists between the first and second images;
   c) if an equivalent value exists between the first and second images, using the location of the pixel having the equivalent value to align the first and second images; and
   d) if an equivalent value does not exists between the first and second images, selecting another spectral wavelength and returning to step b);
subtracting, by the processor, the first co-registered image from the second co-registered image to produce a difference image;
generating, by the processor, a cluster region around a difference region in the difference image;
analyzing, by the processor, the spectral radiance from the cluster region to produce a spectral characteristic curve; and
correlating, by the processor, the spectral characteristic curve against a library to identify the gas plume.

2. The method as recited in claim 1, wherein the analyzing the spectral radiance from the cluster region includes analyzing the spectral radiance from the cluster region at a particular time.

3. The method as recited in claim 1, wherein the analyzing the spectral radiance from the cluster region includes analyzing the spectral radiance from the cluster region in the particular difference image.

4. The method as recited in claim 1, wherein the detector detects spectral radiance in the LWIR range.

5. The method as recited in claim 1, wherein the method further comprises removing elevation effects from the first and second images.

6. The method as recited in claim 1, wherein the first image and the second image each have two dimensions relating to space and a third dimension relating to wavelength of the spectral radiance.

7. The method as recited in claim 6, wherein the co-registering includes, for at least one wavelength, lining up temporally adjacent images with the same origin.

8. The method as recited in claim 1, wherein the library is a gas plume model library.

9. A system for detecting and identifying a gas plume, the system comprising:
   a processor;
   a detector in communication with the processor, the detector effective to scan a region of interest to detect first and second detected spectral radiance data;
   a database in communication with the processor, the database including a library;
   wherein the processor is effective to
   create at least a first image and a second image from the first and second detected spectral radiance data;
   co-register the first and second images to produce a first co-registered image and a second co-registered image, comprising:
      a) selecting a spectral wavelength;
      b) performing a pixel level comparison of the first and second images for the selected spectral wavelength to determine if an equivalent spectral wavelength value exists between the first and second images;
      c) if an equivalent value exists between the first and second images, using the location of the pixel having the equivalent value to align the first and second images; and
      d) if an equivalent value does not exists between the first and second images, selecting another spectral wavelength and returning to step b);
   subtract the first co-registered image from the second co-registered image to produce a difference image;
   generate a cluster region around a difference region in the difference image;
   analyze the spectral radiance from the cluster region to produce a spectral characteristic curve; and
   correlate the spectral characteristic curve against the library to identify the gas plume.

10. The system as recited in claim 9, wherein the processor is further effective to receive a request regarding the region of interest and control the detector to detect the spectral radiance from the region of interest.

11. The system as recited in claim 9, wherein the analyzing the spectral radiance from the cluster region includes analyzing the spectral radiance from the cluster region at a particular time.

12. The system as recited in claim 9, wherein the analyzing the spectral radiance from the cluster region includes analyzing the spectral radiance from the cluster region in the difference image.

13. The system as recited in claim 9, wherein the detector detects spectral radiance in the LWIR range.

14. The system as recited in claim 9, wherein the method further comprises removing elevation effects from the first and second images.

15. The system as recited in claim 9, wherein the first image and the second image each have two dimensions relating to space and a third dimension relating to wavelength of spectral radiance.

16. The system as recited in claim 15, wherein the co-registering includes, for at least one wavelength, lining up temporally adjacent images with the same origin.

17. The system as recited in claim 9, wherein the library is a gas plume model library.

18. A method for detecting and identifying a gas plume, the method comprising:
   receiving, by a processor, a request regarding a region of interest including a gas plume;
   detecting, by a detector in communication with the processor, spectral radiance from the region of interest in the LWIR range to detect first and second detected spectral radiance data;
   creating, by the processor, at least a first image and a second image from the first and second detected spectral radiance data, first image and the second image each have two dimensions relating to space and a third dimension relating to wavelength of the spectral radiance;
   removing, by the processor, elevation effects in the first and second images;
   co-registering, by the processor, the first and second images to produce a first co-registered image and a second co-registered image, the co-registering includes, for at least one wavelength, lining up temporally adjacent images with the same origin, comprising:
      a) selecting a spectral wavelength;
      b) performing a pixel level comparison of the first and second images for the selected spectral wavelength to determine if an equivalent spectral wavelength value exists between the first and second images;

c) if an equivalent value exists between the first and second images, using the location of the pixel having the equivalent value to line up the first and second images; and d) if an equivalent value does not exists between the first and second images, selecting another spectral wavelength and returning to step b);

subtracting, by the processor, the first co-registered image from the second co-registered image to produce a difference image;

generating, by the processor, a cluster region around a difference region in the difference image;

analyzing, by the processor, the spectral radiance from the cluster region at a particular time to produce a spectral characteristic curve; and correlating, by the processor, the spectral characteristic curve against a gas plume library to identify the gas plume.

19. The method as recited in claim 1, further comprising:

tracking movement of the gas plume based on a location and time of the gas plume.

20. The system as recited in claim 9, wherein the processor is further effective to track a movement of the gas plume based on a location and time of the gas plume.

* * * * *